Jan. 1, 1974 W. P. THOMSON Plant Pat. 3,422
CARNATION PLANT
Filed Jan. 24, 1972
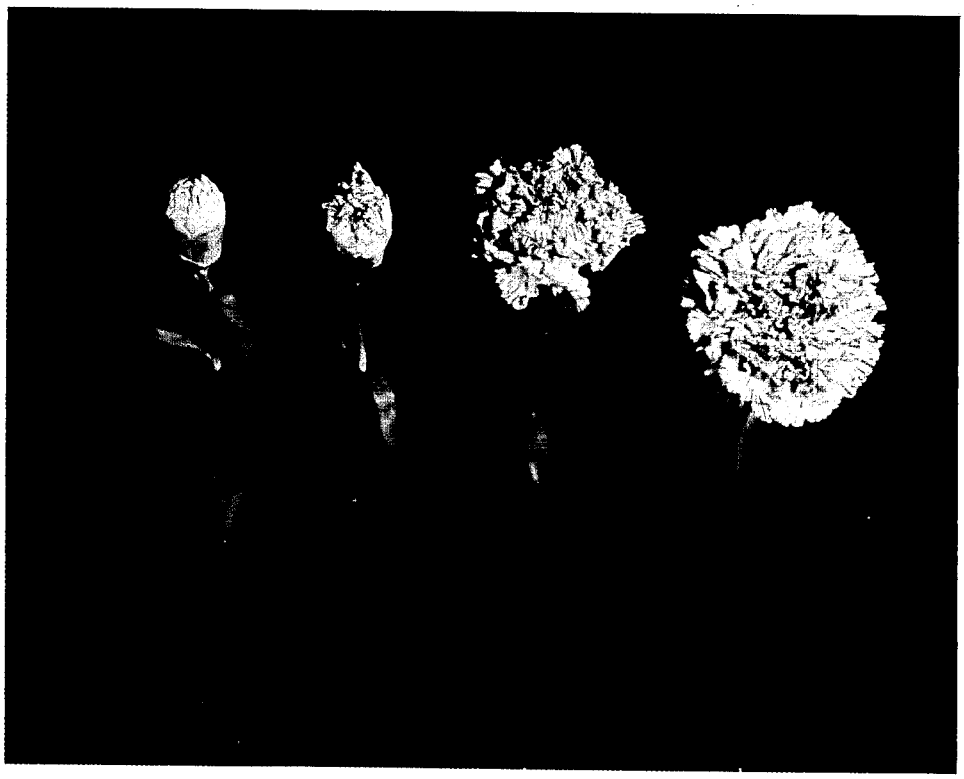
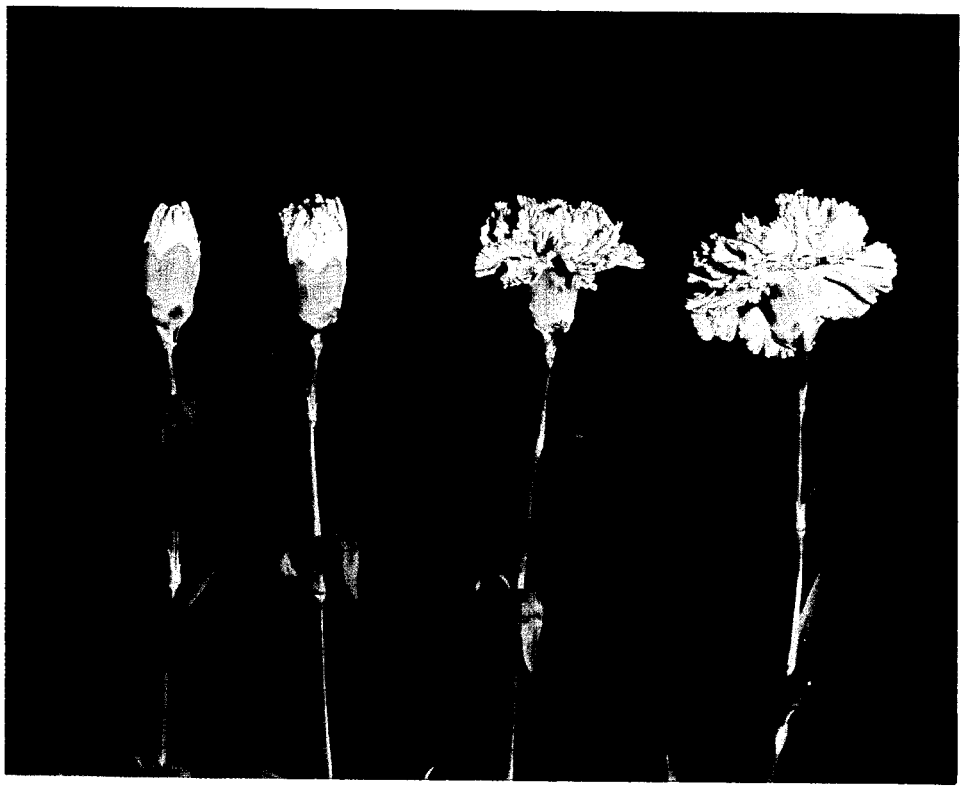

United States Patent Office

Plant Pat. 3,422
Patented Jan. 1, 1974

3,422

CARNATION PLANT

William Pomeroy Thomson, West Hartford, Conn., assignor to The W. W. Thomson Company, Inc., West Hartford, Conn.

Filed Jan. 24, 1972, Ser. No. 220,503
Int. Cl. A01h *5/00*
U.S. Cl. Plt.—70 1 Claim

ABSTRACT OF THE DISCLOSURE

A new variety of carnation plant resulting from meristem propagation of the unpatented variety Barta, the new variety being a sport of Barta and being particularly distinguished from Barta by its larger and better formed flowers which have a more intense coloring, an almost complete absence of splitting, and a taller overall growth.

BACKGROUND OF THE NEW PLANT

My new variety of carnation plant was discovered by me at West Hartford, Conn., in May 1969 as a sport of the variety Barta which was a sport of the variety Lolita (unpatented) which, in turn, originated as a sport of Ember Sim (unpatented). Culture of the meristem of Barta, and propagation by cuttings, produced flowering plants which exhibited the before mentioned distinguishing characteristics and because of the absence of splitting, in particular, which gives the new plant important commercial value, asexual propagation for commercial exploitation has been carried on by greenhouse culture and under my direction at West Hartford, Connecticut. Successive asexually propagated generations of this new variety have all exhibited the same distinguishing characteristics possessed by the original sport and have demonstrated that these characteristics are firmly fixed and hold true from generation to generation.

DESCRIPTION OF THE DRAWINGS

My new variety of carnation plant is illustrated by the accompanying drawings which show the color characteristics of the flower as nearly true as it is reasonably possible to obtain by conventional photographic procedures. The upper view shows the flower development from the bud at first opening to the fully opened bloom as seen from above the specimens; and the lower view shows the same specimens as seen from a lower angle to show the stems, leaves and calyx.

DESCRIPTION OF THE NEW PLANT

The following is a detailed description of the new variety of carnation plant with color designations according to the Methuen Handbook of Colour, second edition, published in 1967 by Methuen & Co. Ltd. of London, England.

*The plant*

Origin: Sport
Parentage: Barta (unpatented)
Classification:
*Botanic.—Dianthus caryophyllus*
*Commercial.*—Carnation
Form: Bush
Height: Normal for Sim varieties
Growth: Vigorous and branching, with strong generally upright stems Foliage: Quantity—normal for Sim varieties with 14 to 18 pairs of leaves per stem
*Leaf size.*—4 to 5 inches long x ½ inch wide
*Shape.*—Curly and long—lanceolate; margin—entire
*Texture.*—Smooth
*Color.*—Upper side—Green, Under side—same as upper side
*Ribs.*—Single rib along center of leaf
*Petioles.*—None. Leaf is decurrent and amplexicaul.

*The bud*

Form: Ovoid
Size: 1 to 1¼ inches tall and ¾ to 1 inch in diameter just before opening
Opening rate: Normal for Sim varieties
Color:
When sepals first divide—Pale Pink 10A3
When petals begin to unfurl—Pink 10A4 with inside appearance of 10A6
Sepals: Spear shaped and stand up from calyx
*Color.*—Pale Green
Calyx:
*Shape.*—Cupped and broad with five upright segments
*Size.*—Large
*Aspect.*—Smooth
*Splitting.*—Practically none—about one percent do split.

*The flower*

Blooming characteristics: Continuous and profusely the year around
Size of bloom: Large. 3¼ to 3¾ inches in diameter and 1¼ to 1½ inches in depth
Borne: Singly—after disbudding
Shape: Generally flat with medium high center and flat outer petals
Petalage: 58 to 64 petals in close imbricated arrangement
*Form.*—Symmetrically round with serrated margins
*Color.*—Both sides of petals have a background of Light Pink 10A4. Upper side has red stripes 10B8 radiating to outer edges of the petals in a non-uniform pattern and a slight blushing to a deeper shade of Pink 10A6 near the base. The base of the petals inside the calyx is of a Light Green color
*Appearance.*—Satiny
Peduncle: ¼ to ½ inch long. Sturdy, upright and of Green color
Discoloration: Pink darkens slightly with age
Effect of weather: Hot weather makes flowers smaller
Fragrance: Slight
Persistence: Flower hangs on and dries
Lasting quality: On plant and as a cut flower—normal for Sim varieties.

*Reproductive organs*

Stamens:
*Anthers.*—Arrangement—upright around ovaries. Length—½ to 1 inch. Number—10 to 12
*Filaments.*—Length—approximately ⅛ inch. Color—White.
*Pollen.*—Yellow in color
Pistils: Number—2; length—1¼ to 1½ inches. Color—White
Stigmas: Color—White
Ovary: Slightly flattened pear-shaped, approximately ¼ x ⅜ inch wide at base and ½ inch high with pointed top. Color—Light Green Fruit: Pear-shaped, fertile, and of Brown color at maturity.

My new variety of carnation plant most nearly resembles its parent Barta and is distinguished by a somewhat taller overall growth and larger flowers. A particular distinction resides in the resistance of the new plant to splitting of the calyx tube when the flower opens. Grown under glass the splitting of the new variety is less than 1% as compared to about 10% for Barta.

I claim:

1. A new and distinct variety of carnation plant, substantially as herein shown and described, characterized by its taller growth and larger flower than its parent Barta and its resistance to splitting upon opening of the flower.

No references cited.

ROBERT E. BAGWILL, Primary Examiner